US00PP34852P2

(12) United States Plant Patent
Scheiber et al.

(10) Patent No.: US PP34,852 P2
(45) Date of Patent: Dec. 20, 2022

(54) ***CARYOPTERIS* PLANT NAMED 'EMERALD CREST'**

(50) Latin Name: ***Caryopteris* hybrid**
Varietal Denomination: Emerald Crest

(71) Applicant: Ball Horticultural Company, West Chicago, IL (US)

(72) Inventors: Sloane Michele Scheiber, Parkesburg, PA (US); Emily E. Alff, Royersford, PA (US); Jessica Diane Janes, Elkton, MD (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/946,234

(22) Filed: Sep. 16, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Caryopteris* plant named 'Emerald Crest', characterized by its medium violet-blue colored flowers, dark green-colored foliage, and moderately vigorous, compact-mounded growth habit, is disclosed.

1 Drawing Sheet

Latin name of genus and species of plant claimed: *Caryopteris* hybrid.

Variety denomination: 'Emerald Crest'.

BACKGROUND OF THE INVENTION

The present invention relates to a new and distinct cultivar of *Caryopteris* plant botanically known as *Caryopteris* hybrid and hereinafter referred to by the cultivar name 'Emerald Crest'.

The new cultivar originated in a controlled breeding program in Cochranville, Pa. during the fall of 2013. The objective of the breeding program was the development of *Caryopteris* cultivars having dark green foliage coloration and a compact-mounded habit.

The new *Caryopteris* cultivar is the result of open-pollination. The female (seed) parent of the new cultivar is the proprietary *Caryopteris* hybrid breeding selection coded X10-1551-1, not patented, characterized by its medium violet-blue colored flowers, medium yellow-green colored foliage, and moderately vigorous, mounded growth habit. The male (pollen) parent of the new cultivar is unknown. The new cultivar was discovered and selected as a single flowering plant within the progeny of the above stated open-pollination during September 2017 in a controlled environment in Cochranville, Pa.

Asexual reproduction of the new cultivar by terminal stem cuttings since September 2017 in Cochranville, Pa. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Emerald Crest' as a new and distinct cultivar of *Caryopteris* plant:

1. Medium violet-blue colored flowers;
2. Dark green-colored foliage; and
3. Moderately vigorous, compact-mounded growth habit.

Plants of the new cultivar differ from plants of the female parent primarily in having darker green-colored foliage and a more compact growth habit.

Of the many commercially available *Caryopteris* cultivars, the most similar in comparison to the new cultivar is BEYOND MIDNIGHT 'CT-9-12', U.S. Plant Pat. No. 27,426. However, in comparison, plants of the new cultivar differ from plants of 'CT-9-12' in at least the following characteristics:

1. Plants of the new cultivar have lighter violet-blue colored flowers than plants of 'CT-9-12'; and
2. Plants of the new cultivar have longer and wider leaves than plants of 'CT-9-12'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Emerald Crest'. The plants were approximately seven months old and grown in 1.7-gallon containers for approximately four months in an outdoor nursery environment in West Chicago, Ill. Plants were given one pinch at approximately two weeks before transplant and another one week after transplant.

DETAILED BOTANICAL DESCRIPTION

Figure 1:
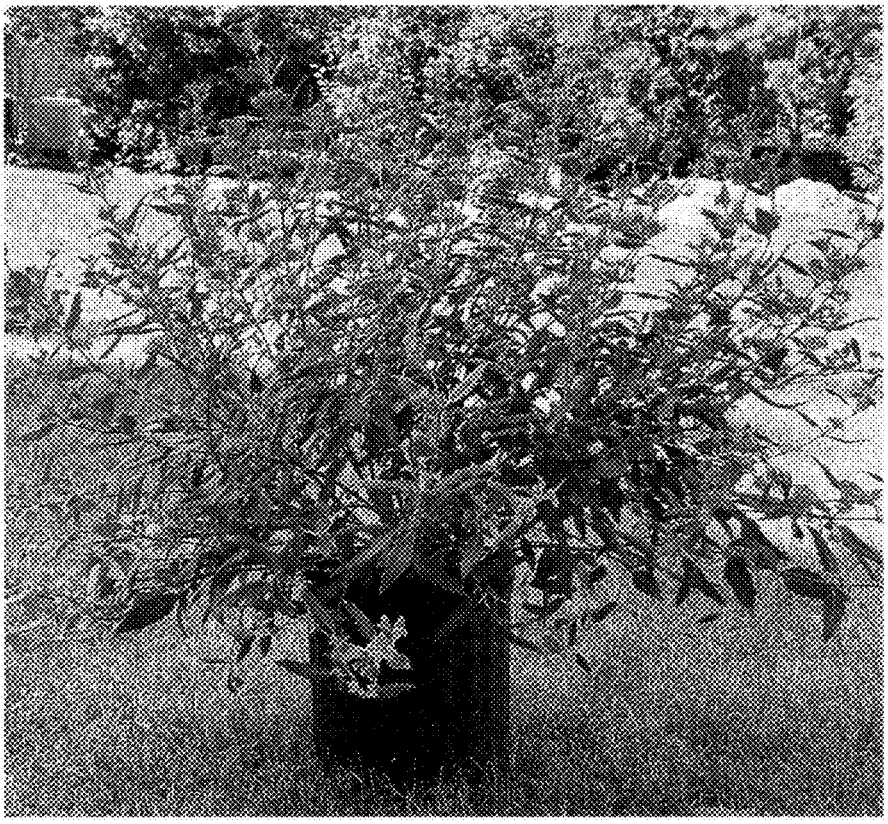
FIG. 1 illustrates a side view of the overall growth and flowering habit of 'Emerald Crest'.
Figure 2:
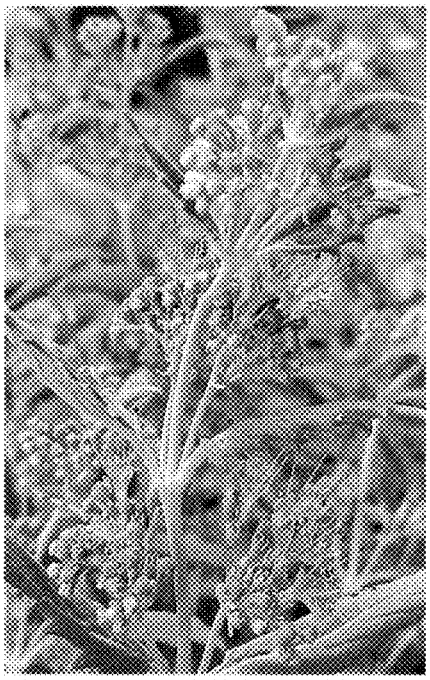
FIG. 2 illustrates a close-up view of inflorescences of 'Emerald Crest'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in September 2022 under natural light conditions in Naperville, Ill.

The following descriptions and measurements describe approximately seven-month old plants produced from cuttings from stock plants and grown in a polycarbonate-covered greenhouse under conditions comparable to those used in commercial practice. Approximately twelve weeks after sticking, rooted plants were transplanted into 1.7-gallon containers utilizing a soilless growth medium. Plants were then transferred to an outdoor nursery environment in West Chicago, Ill. and grown for approximately four months. Plants were given one pinch at approximately two weeks before transplant and another one week after transplant. Prior to transplant plants were grown in liners in a polycarbonate greenhouse in West Chicago, Ill. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Caryopteris* hybrid 'Emerald Crest'.

Parentage:

*Female parent.*—Proprietary *Caryopteris* hybrid breeding selection coded X10-1551-1 not patented.

*Male parent.*—Unknown.

Propagation:

*Type cutting.*—Terminal stem.

*Time to initiate roots.*—Approximately 10 to 12 days.

*Time to produce a rooted cutting.*—Approximately 35 to 42 days.

*Root description.*—Medium to fine.

*Rooting habit.*—Freely branching, moderately dense.

Plant description:

*Commercial crop time.*—Approximately 12 to 14 weeks from a rooted cutting to finish in a 15 cm pot.

*Growth habit and general appearance.*—Perennial, compact-mounded.

*Hardiness.*—USDA Zone 6a (−10° F. to −5° F./−23.3° C. to −20.6° C.).

*Size.*—Height from soil level to top of plant plane: Approximately 56.0 cm. Width: Approximately 91.0 cm.

*Branching habit.*—Freely branching, pinching enhances basal branching. Quantity of main branches per plant: Approximately 18.

*Branch.*—Strength: Strong. Shape: Square in cross section. Length: Approximately 47.0 cm. Diameter: Approximately 4.0 mm. Length of central internode: Approximately 5.0 cm. Texture: Tomentose. Color of young stems: 145B. Color of mature stems: 187A to 187B, becomes woody 199A with age.

Foliage description:

*General description.*—Fragrance: Strong, lavender-like. Form: Simple. Arrangement: Opposite.

*Leaves.*—Quantity per lateral branch: Approximately 20. Aspect: Acute angle to perpendicular to stem. Shape: Narrowly ovate. Margin: Widely serrate. Apex: Acute. Base: Rounded. Venation pattern: Pinnate. Length of mature leaf: Approximately 6.7 cm. Width of mature leaf: 2.6 cm. Texture of upper surface: Puberulent having a velvet-like feel. Texture of lower surface: Densely glandular pubescent. Color of upper surface of young and mature foliage: 137A with 139A, venation of 146D. Color of lower surface of young and mature foliage: 191A with venation of 146D.

*Petiole.*—Strength: Strong, flexible. Aspect: Acute angle to stem. Length: Approximately 1.5 cm. Diameter: Approximately 2.0 mm. Texture: Tomentose. Color: 146D.

Flowering description:

*Flowering habit.*—'Emerald Crest' is a long-day obligate, freely flowering under outdoor growing conditions, blooming from August to October.

*Lastingness of individual inflorescence on the plant.*—Approximately 10 to 14 days.

Inflorescence description:

*General description.*—Type: Terminal and axillary dichasial cymes, self-cleaning. Aspect: Upward and outward. Quantity per plant: Approximately 4 to 12 cymes per branch. Quantity of fully open flowers per inflorescence: Approximately 6 to 8. Height: Approximately 2.2 cm. Diameter: Approximately 3.1 cm. Fragrance: Slight, lavender-like.

*Peduncle.*—Strength: Strong. Aspect: Acute angle to stem. Length: Approximately 1.5 cm. Diameter: Approximately 1.0 mm. Texture: Tomentose. Color: 191A.

*Bud.*—Quantity per inflorescence: Approximately 8 to 10. Rate of opening: Generally takes 3 to 4 days for bud to progress from first color to fully open flower.

*Bud just before opening.*—Shape: Obovoid. Length: Approximately 3.0 mm. Width: Approximately 2.0 mm. Color: 93B.

*Corolla.*—Shape: Bilabiate, upper lip having three lobes and lower lip having two elongated lobes, base fused into a tube. Diameter: Approximately 6.0 mm. Depth: Approximately 7.0 mm.

*Upper lip.*—Shape: Oblong. Margin: Entire. Apex: Rounded. Length from throat: Approximately 2.0 mm. Width: Approximately 1.5 mm. Texture of upper (inner) surface: Glabrous. Texture of lower (outer) surface: Tomentose. Color of upper (inner) surface when first and fully open: 93D. Color of lower (outer) surface when first and fully open: 93C.

*Lower lip.*—Shape: Obovate, cupped. Margin: Fringed. Apex: Obtuse. Length from throat: Approximately 5.0 mm. Width: Approximately 4.0 mm. Texture of upper (inner) surface: Glabrous. Texture of lower (outer) surface: Tomentose in a central longitudinal strip. Color of upper (inner) surface when first and fully open: 93D. Color of lower (outer) surface when first and fully open: 93C.

*Corolla tube.*—Length: Approximately 2.0 mm. Diameter: Approximately 1.5 mm. Texture of inner and outer surfaces: Glabrous. Color of inner and outer surfaces: 93D with base of NN155D.

*Calyx.*—Shape: Cupped. Diameter: Approximately 2.0 mm.

*Sepals.*—Quantity per flower: Approximately 5, fused at base. Shape: Lanceolate. Margin: Entire. Apex: Acute. Length: Approximately 2.5 mm. Width: Less than 1.0 mm. Texture of inner surface: Glabrous. Texture of outer surface: Tomentose. Pubescence color: NN155D. Color of upper and lower surfaces: 146B, outer surface appears lighter due to pubescence.

*Pedicel.*—Strength: Strong, flexible. Aspect: Acute angle to peduncle. Length: Approximately 1.0 mm to 2.0 mm. Diameter: Less than 1.0 mm. Texture: Tomentose. Pubescence color: NN155D. Color: 146C, appears lighter due to pubescence.

*Reproductive organs.*—Androecium: Stamen quantity: 4. Stamen length: Approximately 3.0 mm. Filament color: NN155D. Anther shape: Bi-lobed. Anther length: Approximately 1.0 mm. Anther color: 199A. Pollen amount: None observed. Gynoecium: Pistil quantity: 1 per floret. Pistil length: Approximately 9.0 mm. Stigma shape: Bifid. Stigma length: Less than 1.0 mm. Stigma color: 93B. Style length: Approximately 8.0 mm. Style color: 93D. Ovary diameter: Approximately 1.0 mm. Ovary color: 145A.

Seed and fruit production: Neither seed nor fruit production has been observed.

Disease and pest resistance: Resistance to pathogens and pests common to *Caryopteris* has not been observed.

What is claimed is:

1. A new and distinct cultivar of *Caryopteris* plant named 'Emerald Crest', substantially as herein illustrated and described.

* * * * *